United States Patent
Agano

(10) Patent No.: US 6,462,351 B1
(45) Date of Patent: Oct. 8, 2002

(54) RADIATION IMAGE DETECTING APPARATUS

(75) Inventor: Toshitaka Agano, Kaisei-machi (JP)

(73) Assignee: Fuji Photo Film Co., Ltd., Kanagawa-Ken (JP)

(*) Notice: Subject to any disclaimer, the term of this patent is extended or adjusted under 35 U.S.C. 154(b) by 0 days.

(21) Appl. No.: 09/571,358

(22) Filed: May 15, 2000

(30) Foreign Application Priority Data

May 14, 1999 (JP) .............................. 11-134286

(51) Int. Cl.[7] .............................................. G01N 23/04
(52) U.S. Cl. ................................. 250/580; 250/370.01
(58) Field of Search ............................ 250/580, 584, 250/370.01

(56) References Cited

U.S. PATENT DOCUMENTS

| | | | |
|---|---|---|---|
| 4,733,254 A | * 3/1988 | Yukihiro et al. | ............ 346/140 |
| 4,803,359 A | 2/1989 | Hosoi et al. | ................. 250/327 |
| 5,043,582 A | * 8/1991 | Cox et al. | ............... 250/370.09 |
| 5,187,369 A | 2/1993 | Kingsley et al. | ............ 250/370 |
| 6,049,674 A | * 4/2000 | Yamamoto et al. | ......... 354/290 |

FOREIGN PATENT DOCUMENTS

| | | | | |
|---|---|---|---|---|
| JP | 59-211263 | 11/1984 | ........... | H01L/27/14 |
| JP | 1-216290 | 8/1989 | ............. | G01T/1/24 |
| JP | 2-164067 | 6/1990 | ......... | H01L/27/146 |
| JP | 10-232824 | 9/1998 | ........... | G06F/12/06 |
| JP | 10/271374 | 10/1998 | .......... | H04N/5/225 |
| WO | 92/06501 | 4/1992 | ........... | H01L/27/14 |

* cited by examiner

*Primary Examiner*—Georgia Epps
*Assistant Examiner*—M. Hasan
(74) *Attorney, Agent, or Firm*—Sughrue Mion, PLLC

(57) ABSTRACT

A radiation image detecting apparatus is provided with a solid radiation sensor which detects radiation bearing image information and outputs an electric image signal bearing the image information and an image output section which prints out a visible image on the basis of the image signal output from the solid radiation sensor. The solid radiation sensor and the image output section are housed in a single casing.

7 Claims, 4 Drawing Sheets

F I G. 3
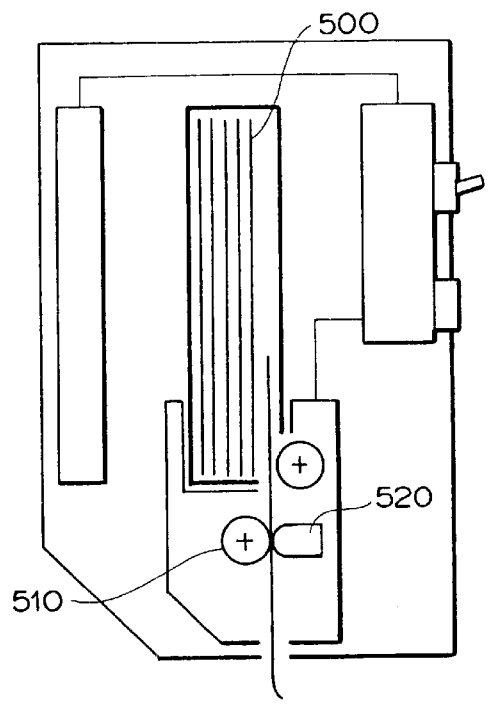
F I G. 4
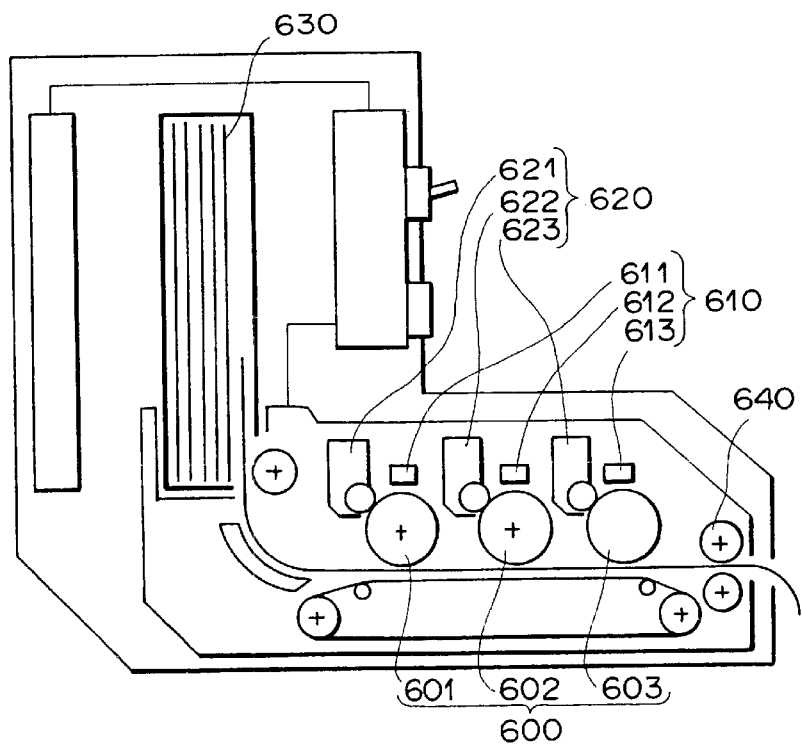

RADIATION IMAGE DETECTING APPARATUS

BACKGROUND OF THE INVENTION

1. Field of the Invention

This invention relates to a radiation image detecting apparatus which detects radiation image information by use of a solid radiation sensor to output an image signal representing a radiation image carried by the radiation image information and prints out a visible image on the basis of the image signal.

2. Description of the Related Art

There have been proposed various radiation image detecting apparatuses provided with a solid radiation sensor which detects radiation carrying thereon radiation image information and outputs an electric image signal representing a radiation image carried by the radiation image information, and an image output section which prints out a visible image on the basis of the electric image signal.

The solid radiation sensor is mainly formed by use of a semiconductor, and converts radiation impinging thereupon directly to electric charges, or converts radiation impinging thereupon once to light by use of phosphor or the like and then converts the light to electric charges. Then the solid radiation sensor once stores the electric charges in a charge storage section and outputs the stored electric charges as an electric image signal representing the image information.

The solid radiation sensors can be classified, for instance, by the process of generating electric charges into light conversion type solid radiation sensors which convert radiation impinging thereupon once to light (fluorescence) by use of phosphor, then convert the light to electric charges by a photoelectric convertor element, once store the electric charges in a charge storage section of the photoelectric convertor element and output the stored electric charges as an electric image signal representing the image information (see, for instance, Japanese Unexamined Patent Publication Nos. 59(1984)-211263 and 2(1990)-164067, and PCT International Publication No. WO92/06501), and a direction conversion type solid radiation sensors which collect signal charges generated in a radiation-conductive material (a material which exhibits electric conductivity upon exposure to radiation) upon exposure to radiation by a charge collecting electrode, once store the collected signal charges in a charge storage section, and convert the stored charges to an electric signal (see, for instance, Japanese Unexamined Patent Publication No. 1(1989)-216290). Further, the solid radiation sensors can be classified by the read-out process of reading out the stored charges into TFT read-out type solid radiation sensors which scan a TFT (thin film transistor) connected to the charge storage section, optical read-out type solid radiation sensors which project reading light (reading radiation) onto a detector, and a so-called improved direct conversion type solid radiation sensors which are combinations of the direct conversion type and the optical read-out type and are proposed in our Japanese Patent Application Nos. 10(1998)-232824 and 10(1998)-271374.

When radiation passing through an object impinges upon such a solid radiation sensor, electric charges are stored in each position on the solid radiation sensor in proportion to the amount of the radiation. The electric charges are detected as an electric signal and the electric signal is output to an image output section, and the image output section prints out, as a visible image, image information carried by the radiation passing through the object.

In the conventional radiation image detecting apparatuses using a solid radiation sensor, the solid radiation sensor and the image output section are separated from each other and are connected through a cable or the like, and a plurality of solid radiation sensors are sometimes connected to one image output section.

However, the system in which the solid radiation sensor and the image output section are separated from each other is disadvantageous in that, when a single operator operates the radiation image detecting apparatus, the operator has to move to the image output section after taking a radiation image at the solid radiation sensor to make preparation for output of an image, return to the solid radiation sensor to output print instruction to the image output section, and then move again to the image output section to take out the print. Accordingly it takes a long time and a lot of labor to obtain a print for diagnosis. Further when the solid radiation sensor and the image output section are separated from each other, wiring is complicated and a large space including those required for operation and maintenance becomes necessary, which deteriorates space utilization efficiency and causes noise due to the wiring and interface trouble due to contact failure and the like, and as a result, cost for maintaining the apparatus is increased.

SUMMARY OF THE INVENTION

In view of the foregoing observations and description, the primary object of the present invention is to provide a radiation image detecting apparatus which is high in space utilization efficiency, allows to easily obtain a radiation image, and is low in both the manufacturing cost and the maintenance cost.

The radiation image detecting apparatus of the present invention comprises a solid radiation sensor which detects radiation bearing thereon image information and outputs an electric image signal bearing thereon the image information, an image output section which prints out a visible image on the basis of the image signal output from the solid radiation sensor, and a single casing which houses the solid radiation sensor and the image output section.

A read-out processing section which carries out read-out processing on the image signal output from the solid radiation sensor, and an output processing section which carries out image output processing on the image signal processed by the read-out processing section may be provided in the casing.

The read-out processing section and the output processing section may be formed by a common processing circuit section.

The image output section may print out the visible image by use of a thermal head system, an exposure/heat-development system, an electrophotography system or an ink jet system.

In accordance with the present invention, since the solid radiation sensor and the image output section are housed in one casing, the operator can perform all the operations from taking a radiation image to output of a visible image in one place, and accordingly, the operator's labor can be saved. Further the space for installing the radiation image detecting apparatus including those required for wiring, maintenance and the like can be narrowed and the space utilization efficiency can be improved. Further since the wiring is simplified, generation of noise due to the wiring and interface trouble due to contact failure and the like can be suppressed, and since a power source and/or a control panel can be made common to the solid radiation sensor and the image output section, the manufacturing cost and the maintenance cost can be reduced.

Further, when the read-out processing and the output processing are performed by a common processing circuit section, the manufacturing cost can be further reduced.

BRIEF DESCRIPTION OF THE DRAWINGS

FIG. 3 is a schematic showing a modification of the embodiment where a thermal head system is employed in the image output section, FIG. 4 is a schematic showing a modification of the embodiment where an electrophotography system is employed in the image output section.

DESCRIPTION OF THE PREFERRED EMBODIMENT

Figure 1:
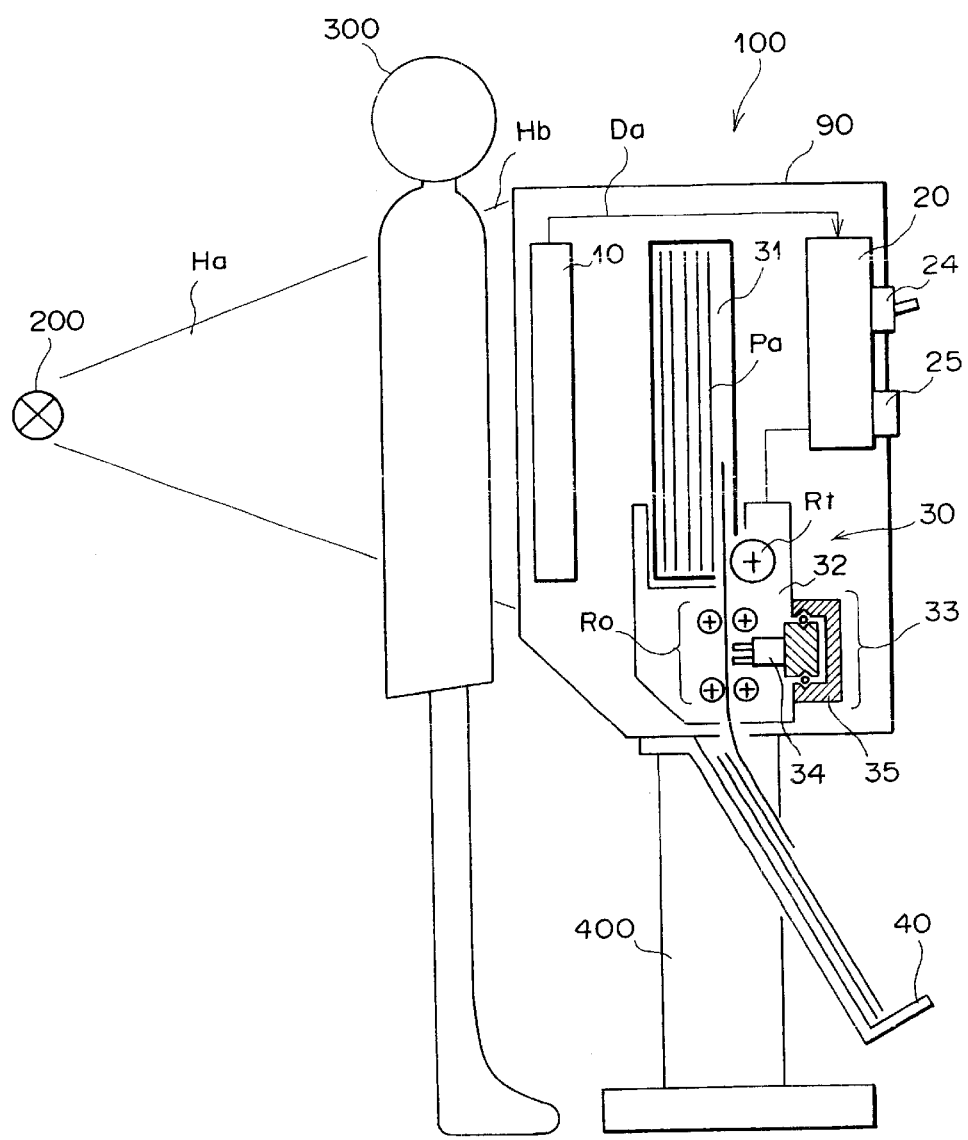
FIG. 1 is a schematic view showing a radiation image detecting apparatus in accordance with an embodiment of the present invention.

In FIG. 1, a radiation image detecting apparatus 100 in accordance with an embodiment of the present invention comprises a solid radiation sensor 10 which detects radiation bearing thereon image information and outputs an electric image signal representing the image information, a controlling section 20 which carries out an image processing on a detected image signal Da output from the solid radiation sensor 10 and controls printing of a visible image based on the processed image signal, an image output section 30, and a casing 90 which houses the solid radiation sensor 10, the controlling section 20 and the image output section 30. The image output section 30 comprises a paper stocker 31, a paper supply mechanism 32 and a printer head 33. The radiation image detecting apparatus 100 is supported on an adjustable stand 400 which adjusts the level of the radiation image detecting apparatus 100 according to the part of an object 300 to be radiographed.

Figure 2:
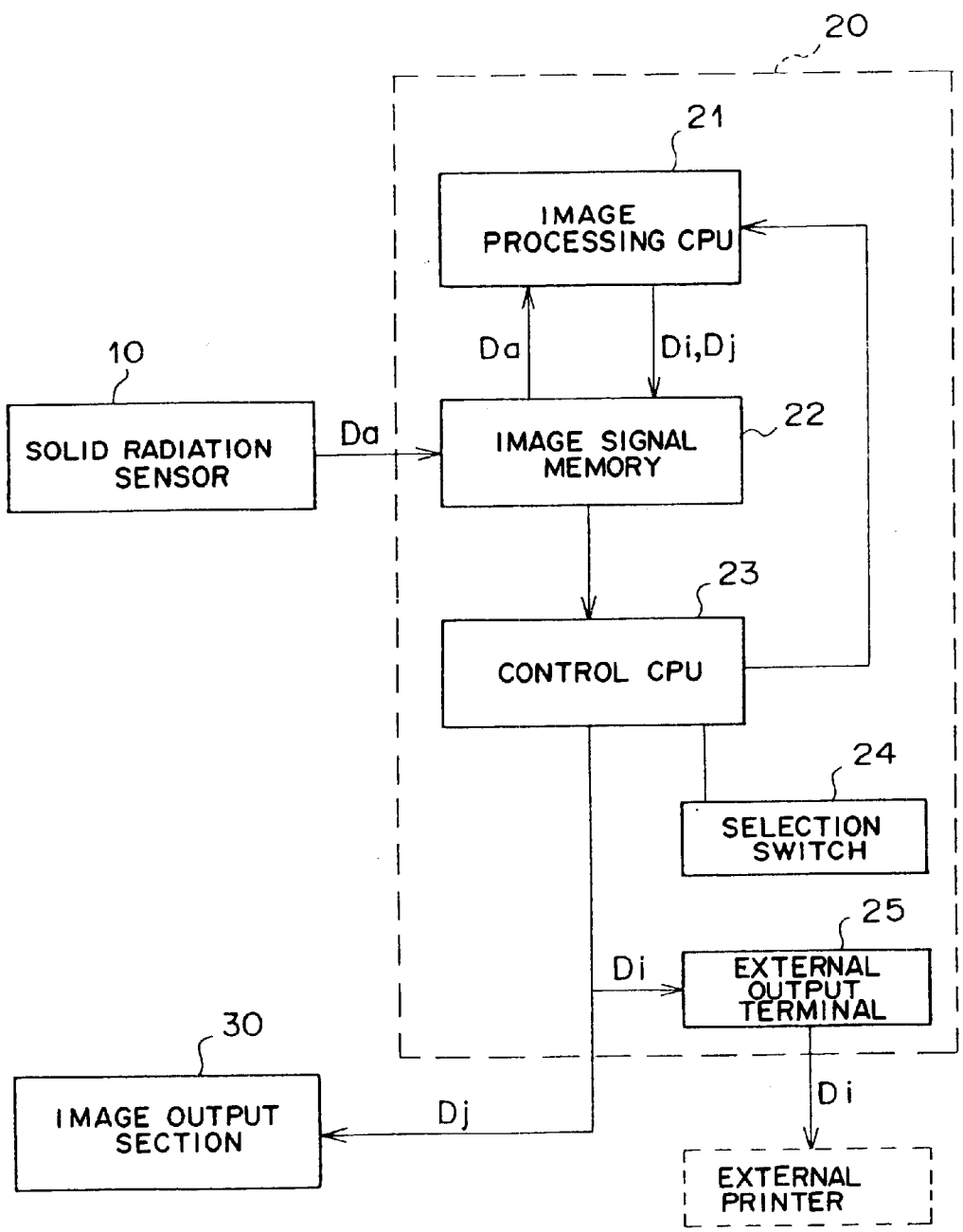
FIG. 2 is a view showing in detail the processing performed by the controlling section.

As shown in FIG. 2, the controlling section 20 comprising an image processing CPU 21 into which the detected image signal Da output from the solid radiation sensor 10 is input by way of an image signal memory 22 to be described later and which has function to carry out read-out processing on the detected image signal Da and output a processed read-out image signal Di and function to carry out output processing on the processed read-out image signal Di and output a processed output image signal Dj, and an image signal memory 22 which temporarily stores the detected image signal Da, the processed read-out image signal Di and the processed output image signal Dj, a selection switch 24 for setting whether printing is to be made by the built-in image output section 30 or by an external printer, and a control CPU 23 which controls printing. When that printing is to be made by an external printer is selected by the selection switch 24, the control CPU 23 takes out the processed read-out image signal Di from the memory 22 and outputs it to the external printer through an external output terminal 25. When that printing is to be made by the built-in image output section 30 is selected by the selection switch 24, the control CPU 23 takes out the processed output image signal Dj from the memory 22 and outputs it to the built-in image output section 30 so that the built-in image output section 30 prints out a visible image on the basis of the processed output image signal Dj.

In this particular embodiment, the image output section 30 is of an ink jet system. A plurality of printing papers Pa are stored in the paper stocker 31, and the paper supply mechanism 32 comprises a paper takeout roller Rt which takes out the printing papers Pa one by one from the paper stocker 31, and conveyor rollers Ro which convey the printing paper Pa at a constant speed and discharge it to a print stocker 40 outside the radiation image detecting apparatus 100. The printer head 33 comprises an ink discharge head 34 which is provided with a low gradation nozzle which discharges ink for low gradation to print a low gradation portion of the image and a high gradation nozzle which discharges ink for high gradation to print a high gradation portion of the image, an ink discharge head scanning mechanism 35 which causes the ink discharge head 34 to scan the printing paper Pa in a direction transverse to the direction in which the printing paper Pa is conveyed, a low gradation ink cartridge (not shown) which supplies low gradation ink to the low gradation nozzle, and a high gradation ink cartridge (not shown) which supplies high gradation ink to the high gradation nozzle.

Operation of the radiation image detecting apparatus 100 of this embodiment will be described, hereinbelow.

Radiation Ha emitted from a radiation source 200 is projected onto the object 300, and radiation Hb which passes through the object 300 and bears thereon radiation image information impinges upon the solid radiation sensor 10. Upon exposure to the radiation Hb, the solid radiation sensor 10 converts the radiation Hb to an electric image signal representing the radiation image information (detected image signal Da), and outputs the detected image signal Da. The detected image signal Da is input into the controlling section 20 and stored in the image signal memory 22.

When printing by the built-in image output section 30 has been selected by the selection switch 24, the control CPU 23 instructs the image processing CPU 21 to output the processed output image signal Dj to the image signal memory 22. Upon receipt of the instruction from the control CPU 23, the image processing CPU 21 takes out the detected image signal Da stored in the image signal memory 22, carries out the read-out processing on the detected image signal Da to convert it to a processed read-out image signal Di, carries out the output processing on the processed read-out image signal Di to convert it to a processed output image signal Dj, and outputs the processed output image signal Dj to the image signal memory 22.

The processed output image signal Dj input into and stored in the image signal memory 22 is read out by the control CPU 23. The control CPU 23 controls feed of the printing paper Pa by the paper supply mechanism 32 and the amounts of low gradation ink and high gradation ink to be discharged from the ink discharge head 34 according to the processed output image signal Dj, thereby printing a visible image on the printing paper Pa. The printing paper Pa printed with the visible image is discharged to the print stocker 40 outside the radiation image detecting apparatus 100.

When printing by an external printer has been selected by the selection switch 24, the control CPU 23 instructs the image processing CPU 21 to output the processed read-out image signal Di to the image signal memory 22. Upon receipt of the instruction from the control CPU 23, the image processing CPU 21 takes out the detected image signal Da stored in the image signal memory 22, carries out the read-out processing on the detected image signal Da to convert it to a processed read-out image signal Di, and outputs the processed read-out image signal Di to the image signal memory 22.

The processed read-out image signal Di input into and stored in the image signal memory 22 is read out by the control CPU 23 and outputs to an external printer by way of the external output terminal 25. The external printer receives the processed read-out image signal Di and prints a visible image on the basis of the processed read-out image signal Di. The processed read-out image signal Di is standardized to conform to common printers.

The image processing CPU 21 and the control CPU 23 may be replaced with a microprocessor.

The image output section 30 may be of a thermal head system, an exposure/heat-development system, an electro-photography system without being limited to the ink jet system employed in the embodiment described above.

FIG. 3 shows a modification of the embodiment described above where a thermal head system image output section is employed. As shown in FIG. 3, in this modification, thermal recording media 500, each comprising a film coated with a heat-sensitive color producing material layer which produces color upon exposure to heat, are used. Each thermal recording medium 500 is conveyed by a platen roller 510 which pinched between the platen roller 510 and a thermal head 520 having an array of a plurality of heater elements. While the thermal recording medium 500 is conveyed, the heater elements are selectively energized and a visible image is thermally formed on the thermal recording medium 500.

FIG. 4 shows another modification of the embodiment described above where an electrophotography system image output section is employed. In this modification, a latent image is formed on a photosensitive drum 600 by projecting light emitted from, for instance, an LED array 610 onto the drum 600. Then the latent image is developed by toner supplied from a toner cartridge 620. Then the toner image is transferred to a printing paper 630 and fixed by a heated fixing roller 640. In this particular modification, three different sizes of toner are employed according to the density range of the image to be printed, whereby the printable density range can be greatly widened. That is, three toner cartridges 621, 622 and 623 in which different sizes of toner are placed, and three LED arrays 611, 612 and 613 and three photosensitive drums 601, 602 and 603 are provided for the respective toner cartridges 621, 622 and 623.

Figure 5:
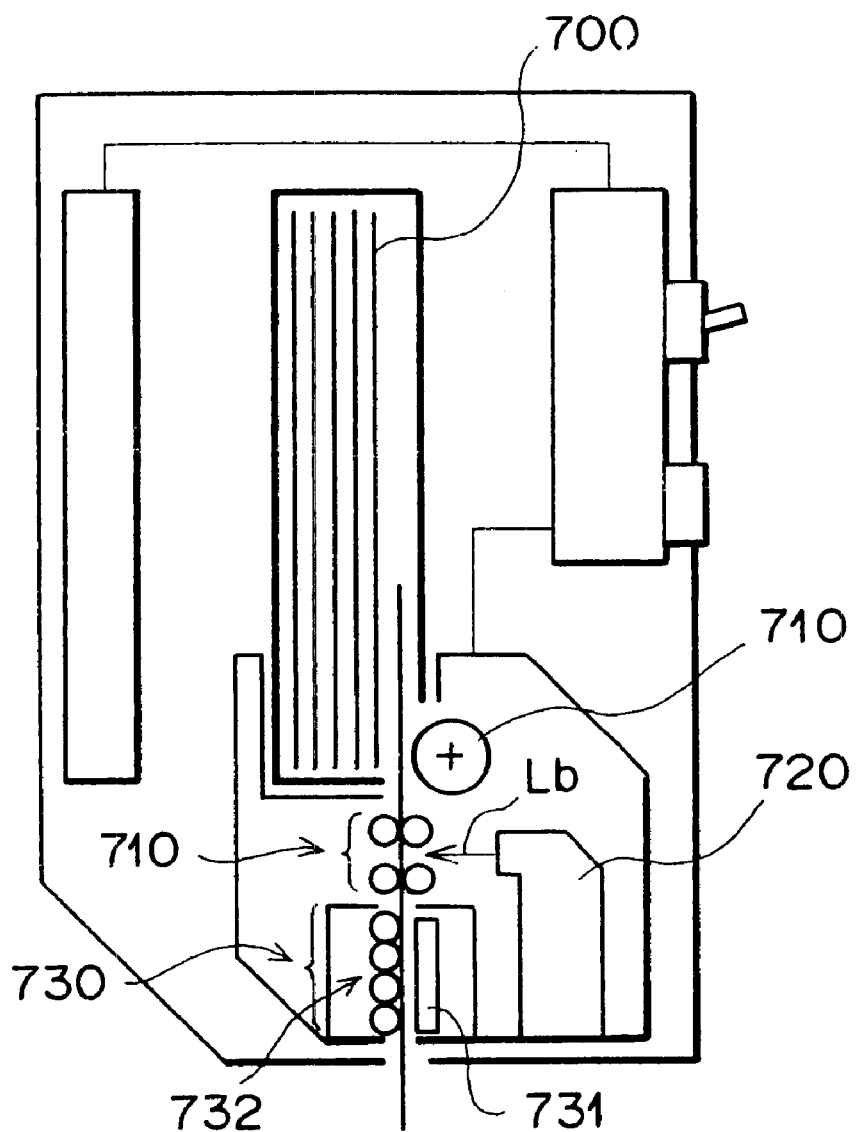
FIG. 5 is a schematic showing a modification of the embodiment where an exposure/heat-development system is employed in the image output section.

FIG. 5 shows still another modification of the embodiment described above where an exposure/heat-development system image output section is employed. In this modification, thermal development photosensitive sheets 700 are employed as the printing media. The thermal development photosensitive sheet 700 is a sheet on which a latent image is formed upon exposure to light and the latent image on which is developed and fixed upon exposure to heat. While the thermal development photosensitive sheet 700 is conveyed by conveyor rollers 710, a laser beam Lb is caused to scan the sheet 700 by a laser scanner unit 720, whereby a latent image is formed on the sheet 700. Then the latent image is thermally developed and fixed by a thermal development section 730 comprising a plate heater 731 and a plurality of press rollers 732 which convey the sheet 700 while pressing the sheet 700 against the plate heater 731.

The read-out processing is processing for correcting the image signal as detected by the solid radiation sensor, which has various features resulting from the properties of the solid radiation sensor used, to an image signal which can be dealt with a general purpose printer and includes an offset correction, a gain correction, a logarithmic conversion, a shading correction, a defective picture element correction and the like.

The offset correction is for compensating for a phenomenon that an image having a certain value is output from the solid radiation sensor though no radiation impinges upon the solid radiation sensor, which would result in an image which is dark as a whole. In the offset correction, the entire image signal is lowered in density by subtracting an offset value from each of the image signal components representing the picture elements of the image so that all the image signal components fall within a predetermined density range.

The gain correction is processing for reducing differences in density range (the difference between the maximum value and the minimum value of the image signal component) among picture elements by multiplying the values of the image signal components for the respective picture elements by a predetermined constant and, thereby, narrowing or widening the density ranges since when the amplification degree to the image signal components differs from picture element to picture element.

The logarithmic conversion is a correction to enhance the contrast of a region which is low in density by, for instance, converting the low density region with a narrower quantizing interval so that more gradation ranges are allotted to the low density region and by converting a high density region with a wider quantizing interval so that less gradation ranges are allotted to the high density region.

The shading correction is a correction which is carried out, for instance, when the strength of the radiation is nonuniform by the area exposed to the radiation or when the sensitivity of the solid radiation sensor is nonuniform by the area exposed to the radiation, to remove unevenness in density (shading) read out in addition to an image signal which would be normally read out.

The defective picture element correction is a correction to interpolate image signal components for abnormal detecting positions of the solid radiation sensor, in which electric charges cannot be detected nor stored, on the basis of the image signal components for normal detecting positions of the solid radiation sensor.

The output processing is processing for correcting the read-out processed image signal according to the properties of the image output section so that a proper visible image can be printed out and includes a shading correction, a printer head temperature correction, a sharpness correction, a black ratio correction and a gradation correction. Though somewhat differing by the printing system, the contents of these corrections are substantially as follows.

The shading correction is for correcting unevenness in density generated due to the properties of the particular printer used.

The printer head temperature correction is for suppressing deterioration in image quality due to change in electric properties, expansion of the structural members, change in physical properties of ink and/or toner which will result from increase in the temperature of the printer head while the printer head is kept operated. For example, in the case of the thermal head or the LED array, the electric properties of the plurality of elements change with temperature, and in the case of the ink jet system, when the diameter of the orifice of the ink discharge nozzle is enlarged or the viscosity of the ink is reduced as the temperature increases, the amount of ink discharged from the ink discharge nozzle changes. The influence of these phenomena should be compensated for.

The sharpness correction is for enhancing high frequency components of spatial frequencies. For example, lines, edges or the like where a pattern of density change is continuous are enhanced by use of differential values of density change.

The black ratio correction is for correcting influence on density of voltage drop for each recording element in a printer head having a plurality of recording elements like a thermal head or an LED array which voltage drop is generated, when a particular recording element consumes a large amount of current, that is, when the density of a particular area is extremely high as compared with that around the particular area, in recording elements in electric relation with the particular recording element.

The gradation correction is for converting the values of the image signal components according to the gradation specification of the printer (e.g., 256 gradations or 1024 gradations) or for converting the values of the image signal components so that the density distribution becomes uniform (e.g., so that the histogram is flattened) when the density is partial to a particular area.

As can be understood from the description above, in accordance with the embodiment described above, since the solid radiation sensor and the image output section are housed in one casing, the operator can perform all the operations from taking a radiation image to output of a visible image in one place, and accordingly, the operator's labor can be saved. Further the space for installing the radiation image detecting apparatus including those required for wiring, maintenance and the like can be narrowed and the space utilization efficiency can be improved. Further since the wiring is simplified, generation of noise due to the wiring and interface trouble due to contact failure and the like can be suppressed, and since a power source and/or a control panel can be made common to the solid radiation sensor and the image output section, the manufacturing cost and the maintenance cost can be reduced. Further, by performing the read-out processing and the output processing by a common processing circuit section, the manufacturing cost can be further reduced.

What is claimed is:

1. A radiation image detecting apparatus comprising a solid radiation sensor which detects radiation bearing thereon image information and outputs an electric image signal bearing thereon the image information, an image output section which prints out a visible image on the basis of the image signal output from the solid radiation sensor, and a single casing which houses the solid radiation sensor and the image output section.

2. A radiation image detecting apparatus as defined in claim 1 in which a read-out processing section which carries out read-out processing on the image signal output from the solid radiation sensor, and an output processing section which carries out image output processing on the image signal processed by the read-out processing section are provided in the casing.

3. A radiation image detecting apparatus as defined in claim 2 in which the read-out processing section and the output processing section are formed by a common processing circuit section.

4. A radiation image detecting apparatus as defined in claim 1 in which the image output section prints out the visible image by use of an ink jet system.

5. A radiation image detecting apparatus as defined in claim 1 in which the image output section prints out the visible image by use of a thermal head system.

6. A radiation image detecting apparatus as defined in claim 1 in which the image output section prints out the visible image by use of an electrophotography system.

7. A radiation image detecting apparatus as defined in claim 1 in which the image output section prints out the visible image by use of an exposure/heat-development system.

* * * * *